United States Patent [19]

Cort et al.

[11] Patent Number: 4,829,051
[45] Date of Patent: May 9, 1989

[54] N-SUBSTITUTED DERIVATIVES OF 1-DESAMINOVASOPRESSIN

[75] Inventors: Joseph H. Cort, Tucson, Ariz.; Alan J. Fischman, Brooklyn, N.Y.

[73] Assignee: Vega Laboratories, Inc., Tucson, Ariz.

[21] Appl. No.: 672,167

[22] Filed: Nov. 16, 1984

Related U.S. Application Data

[63] Continuation of Ser. No. 482,242, Apr. 5, 1983, which is a continuation-in-part of Ser. No. 357,611, Mar. 12, 1982.

[51] Int. Cl.$^4$ .......................... A61K 37/34; C07K 7/16
[52] U.S. Cl. ........................................... 514/11; 514/8; 514/807; 530/315
[58] Field of Search ................... 260/112.5 R; 514/11, 514/8, 807; 530/315

[56] References Cited

U.S. PATENT DOCUMENTS

| 3,497,491 | 2/1970 | Zaoral et al. | 260/112.5 R |
| 3,558,590 | 1/1971 | Cort et al. | 260/112.5 R |
| 3,980,631 | 9/1976 | Prochazka et al. | 260/112.5 R |
| 4,180,501 | 12/1979 | Coy et al. | 260/112.5 R |

OTHER PUBLICATIONS

Hechter, *J. Biol. Chem.*, 253, 3230, (1978).
Bippi, "Peptidsynthesin Am Lysin-Vasopressin", Diplomarbeit, University of Hohenheim, Germany, (1980).

*Primary Examiner*—Delbert R. Phillips
*Attorney, Agent, or Firm*—Kenyon & Kenyon

[57] ABSTRACT

Novel analogs of biologically active vasopressin and its synthetic analogs having improved activity are represented by the structural formula:

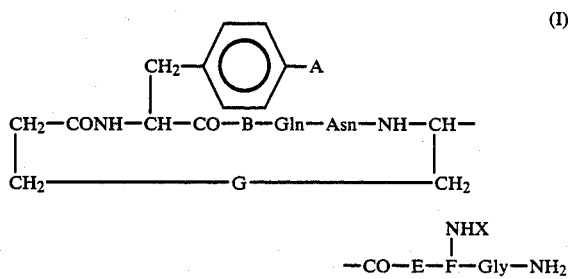

wherein A hydrogen; is hydroxy or lower alkoxy, especially methoxy, B is the peptide residue of phenylalanine (Phe) or isoleucine, Gln represents the peptide residue of glutamine Asn represents the peptide residue of asparagine, E represents the peptide residue of proline (Pro), 4-thioproline (4-thioPro) or 3,4-dehydroproline (3,4-dehydroPro), FNH represents an N-substituted peptide residue of L- or D-lysine (Lys) L or D homolysine (h Lys) or L- or D-orntihine (Orn), X represents a side peptide chain consisting of one or more of Gly, L-Ala, L-Val, L-Leu, or L-Phe, Gly represents the peptide residue of glycine, and G is disulfide (—S—S—) or thioether (—CH$_2$S— or —SCH$_2$—).

7 Claims, No Drawings

N-SUBSTITUTED DERIVATIVES OF 1-DESAMINOVASOPRESSIN

CROSS-REFERENCE TO RELATED APPLICATIONS

This application is a continuation of application Ser. No. 482,242, filed 4/5/83, which is a continuation-in-part of Ser. No. 357,611, 3/12/82.

BACKGROUND OF THE INVENTION

The present invention relates to novel biologically-active vasopressin analogs. More particularly, the invention is concerned with vasopressin and its biologically-active polypeptide analogs which have been modified to produce long-acting forms of the polypeptides and are believed to function by slow release of an active vasopressin or vasopressin analog.

It has long been recognized that naturally formed vasopressin has biological effects, such as its antidiuretic activity and its vasoconstriction of visceral blood flow. Its utility, however, is limited by its relatively short half-life in the blood stream, as well as its well known general circulatory systemic pressor effect. Accordingly, a variety of analogs of vasopressin have been synthesized in an effort to modify the properties of vasopressin and provide products having increased pharmaceutical utility.

Efforts to extend the half-life of vasopressin involve modifications intended to inhibit enzymatic cleavage and consequent inactivation of the vasopressin molecule. For example, modification of vasopressin by deamination of cysteine at the 1 position and replacement of L-arginine by the D-isomer at postion 8 yields "desmopressin," which is immune to enzymatic cleavage of the 1-2 and 8-9 carbon-nitrogen bonds. As a consequence, desmopressin has been found to have enhanced and prolonged antidiuretic activity with low pressor activity. See U.S. Pat. No. 3,497,491. In a further modification, replacement of the disulfide bridge with a thioether linkage (—CH$_2$S— or —SCH$_2$—) yields still other analogs having even greater potency and half-life, but without changing the biological target organs of the basic 1-desamino-vasopressin hormone. See U.S. Pat. No. 3,980,631.

Still another approach to new and potentially more effective vasopressin analogs is the preparation of hormonogen forms, i.e., vasopressin analogs having a chain of cleavable peptide residues attached to the active molecule. These analogs are thought to serve as reservoirs of the active molecule, which is slowly released by enzymatic cleavage of the added residues. This approach has so far involved a series of analogs obtained by attachment of one or more peptide residues to the N-terminal of the molecule, as is shown in U.S. Pat. No. 3,558,590. Of these analogs, N$^\alpha$-(glycyl-glycyl-glycyl)-8-lysine-vasopressin, or tGLVP, is of principal interest. Although this modification has been effective in providing a longer-lasting agent, it still is not as effective as desired. For example, cleavage of the hormonogen also occurs at various sites in the active nonapeptide portion of the molecule, so that only a small fraction of the administered tGLVP is actually released in active form. As a result, large doses of tGLVP are required.

The N-terminal NH$_2$ group is, however, not the only possible site of attachment of added residues to form a hormonogen. If a basic residue such as Lys, homoLys or Orn is used at amino acid position 8, the resulting (N$^\Omega$)-NH$_2$ group at this position may also be useful as an attachment site.

Hechter et. al. (J. Biol. Chem. 253: 3230-3236, 1978) has reported on the use of [8-Lys-N$^\epsilon$-(Gly)]-vasopressin in a structure-activity study of adenyl cyclase activation in renal homogenate material. Bippi, "Peptidsynthesin am Lysin-Vasopressin", Diplomarbeit, University of Hohenheim, Germany, published April, 1980 has prepared similar peptides, i.e., [8-Lys-N$^\epsilon$-(X)]-vasopressin wherein X is Gly or Phe. A hormonogen of this type, however, would be expected to be metabolized and inactivated quickly since it contains a primary site for aminopeptidase action, the (N$^\alpha$)NH$_2$ group of the cysteine residue at position 1.

It thus would be desirable to modify vasopressin and its biologically active analogs in a similar but novel manner to prolong "release" of the active polypeptide in sufficient "yield" to permit the use of relatively smaller doses.

SUMMARY OF THE INVENTION

It is, therefore, an object of the present invention to provide novel polypeptide analogs of vasopressin.

It is a further object of this invention to provide novel hormonogens of vasopressin and its analogs.

Still another object of this invention is the provision of long-acting polypeptide vasopressin analogs.

Another object of this invention is the provision of long-acting polypeptide hormonogen analogs which have greater activity than the known long-acting hormonogen vasopressin analogs.

These and other objects are achieved by the invention which is directed to hormonogen forms of novel vasopressin analogs which have enhanced activity and a long effective lifetime. According to the invention, the hormonogens are polypeptides which may be represented by formula I

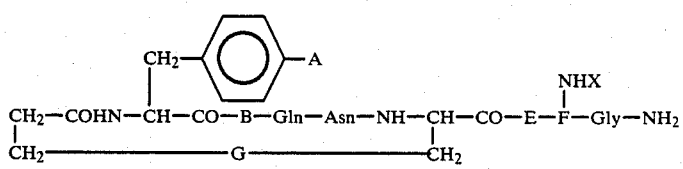

wherein A represents hydrogen, hydroxy or alkoxy of 1 to 5 carbons, especially methoxy; B represents a peptide residue of phenylalanine (Phe) or isoleucine (Ile); Gln represents a peptide residue of glutamine; Asn represents a peptide residue of asparagine, E represents a peptide residue of proline (Pro), 4-thioproline (4-thio-Pro) or 3,4-dehydroproline (3,4-dehydroPro); F-NH represents a residue of D or L-lysine (Lys) D-or L-homolysine (hLys) or D or L-ornithine (Orn); Gly represents a peptide residue of glycine; G represents a disulfide (—S—S—) or thioether (—CH$_2$S— or —SCH$_2$—) group and X represents a peptide side chain of from 1 to 5 saturated or aromatic alpha-amino acid reidues.

In the context of the present invention, a "peptide residue" is the divalent moiety obtained upon the removal of hydrogen from the alpha amino group and the hydroxyl group from the carboxyl group of an alpha-amino acid. Also, in the context of the present invention, a saturated or aromatic alpha-amino acid residue similarly is the peptide coupling moiety formed from an alpha-amino acid of the formula $H_2NCHRCO_2H$ wherein R is hydrogen, an aliphatic group or an aromatic group.

Preferred amino acid residues which can be used for the peptide side chain X are those derived from glycine (Gly), alanine (Ala), valine (Val), leucine (Leu), isoleucine (Ile) and phenylalanine (Phe). Residues other than the Gly residue are in the L-configuration. The glycine residue is especially preferred, with the tripeptide Gly-Gly-Gly chain being most preferred as the peptide side chain.

The preferred number of amino acid residues present in the peptide side chain is from 1 to 3 with 2 or 3 residues being especially preferred.

The hormonogens of the invention are pro-drug forms of 1-desamino-vasopressin analogs having a basic peptide residue at position 8. These 1-desaminovasopressin analogs may be represented by formula II

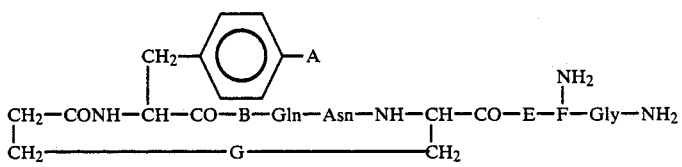

wherein A, B, E, and G are as defined in the foregoing discussion and F—NH$_2$ corresponds to the form of F—NHX as defined in the foregoing discussion wherein hydrogen has replaced X.

Preferred hormonogens of foregoing formula I include those wherein F is L-or D-Lys or L-or D-Orn, B is Phe, E is Pro and G is disulfide. A particularly preferred hormonogen of formula I is one wherein F is L-Lys.

Especially preferred hormonogens of formula I include those wherein:

A is hydrogen, B is Phe, E is Pro, F is L-Lys, G is disulfide and X is Gly, Gly-Gly, or Gly-Gly-Gly.

The invention also directed to a pharmaceutical composition and a method for minimizing or preventing gastrointestinal, visceral or uterine bleeding in a patient suffering such distress. The composition is a combination of a pharmaceutical carrier and an amount of a hormonogen polypeptide of formula I which effectively minimizes or prevents gastrointestinal bleeding, uterine bleeding, bleeding during abdominal or gynecological surgery and controls blood pressure changes associated with burns and hemorrhage. The method is administration to a patient of an amount of a hormonogen polypeptide of formula I which effectively minimizes or prevents gastrointestinal bleeding, uterine bleeding and bleeding during abdominal or gynecological surgery and controls blood pressure changes associated with burns and hemorrhagic shock.

DETAILED DESCRIPTION OF THE INVENTION

The 1-desamino-vasopressin hormonogen polypeptides of the invention are 1-desamino-vasopressin analogs with a basic peptide residue at position 8 to which has been coupled a peptide side chain of 1 to 5 saturated or aromatic amino acid residues. The hormonogen polypeptides provide physiological effects like those of desamino-vasopressin, but in addition have enhanced activity and a long duration of action as shown by the Examples which follow.

Although it is not necessary for the purposes of the invention, it may be theorized that a 1-desamino-vasopressin analog having a basic peptide residue, such as the FNH$_2$ residue at the 8-position of Formula II, is susceptible to enzymatic attack at the basic residue by a trypsin-like enzyme. These enzymes will sever the polypeptide chain at an adjacent carbon-nitrogen bond. It is believed further, that when one omega-terminal amine proton (hydrogen) of this basic peptide residue is substituted by a peptide side chain, the resulting hormonogen does not substantially undergo such cleavage. It is also believed that a peptide side chain joined to a terminal amino group of the 8 position peptide residue of an analog of formula II can be removed by aminopeptidases, thereby releasing the active 1-desamino-vasopressin analog.

The peptide side chain of the hormonogen polypeptides of the invention, then, functions as a protecting group which prevents immediate metabolism or deactivation of the incipient 1-desamino-vasopressin analog when the hormonogen is administered in vivo. The hormonogen acts as a reservoir for sustained production of the active drug, the 1-desamino-vasopressin analog, by slow amino peptidase cleavage of the peptide side chain. Thus, use of the hormonogen will produce physiological activity similar to that of the incipient 1-desamino-vasopressin analog present in the hormonogen and, in addition, will exhibit a longer drug effect.

The hormonogen polypeptides of the invention can readily be prepared by conventional techniques for the synthesis of polypeptides. Such techniques include, for example, stepwise amide coupling of the appropriate amino acids by an activated carbonyl group reaction using such reagents as pivaloyl chloride, N,N-diimidazole carbonyl, mixed anhydride, dicyclohexyl carbodiimide and the like and using amino group and carboxyl group blocking agents such as t-butyloxycarbonyl, carbobenzyloxy, benzyl ester, t-butyl ester and the like.

In a typical preparative scheme, the C-terminal amino acid is blocked at the carboxylic acid group with an appropriate blocking agent and the next amino acid in the peptide sequence is coupled through a coupling reaction using a reagent such as dicyclohexylcarbodiimide. An activated carbonyl group of the N-blocked amino acid, which is next in the sequence, is first formed with the reagent, and then it is reacted with the blocked C-terminal amino acid to form the desired amide bond. The process is repeated with appropriate protected amino acids until the amino acid sequence is finished. Intermediate peptide products can be purified by gel filtration such as use of aqueous swelled cross-linked dextrin gel.

A preferred procedure involves step-wise solid phase synthesis, as described by Stewart and Young in "Solid Phase Peptide Synthesis", W. H. Freeman & Co., San Francisco (1969). In general, this procedure employs a series of functional group blocking and deblocking steps and amide coupling steps as described in the foregoing discussion to build the peptide chain. In addition, however, the appropriate C-terminal amino acid is chemically bonded to a solid, reactive resin so that the subsequent amide bond reactions take place at a liquid-solid interface on the resin. The advantages of this synthesis are speed, efficacy easier removal of impurities since the desired product is bound and can be washed with solvent to remove impurities. The examples explain this procedure in more detail.

Natural vasopressin has a wide spectrum of biological activities, all of which can find clinical use provided that (a) the desired activity is not overwhelmed by other activities which are undesired side-effects and (b) the duration of activity fits the biological needs of the patient in therapy.

Knowledge about the useful biological attributes of a known hormonogen form of vasopressin in therapy, tGLVP, can be summarized as follows.

A. Management of Gastrointestinal Bleeding From Esophageal Varices, Peptic Ulcers, Gastritis, Diverticuli Natural vasopressin hormones show marked vasoconstrictive actions on the entire gut from the lower third of the esophagus to the rectum, on the pancreas and on the uterus in experimental animals at bolus doses of 10-100 ng/kg, but all the blood flow responses are of very short duration. In comparison in the same preparations, tGLVP, because of its low efficiency of active substance delivery, must be given in doses of 20-50 microg/kg for an equipotent response amplitude, but the responses are prolonged considerably. See J. H. Cort, et. al., *Europ. J. Clin. Invest.* 5: 165-175, 1975; and P. Wolfson, et al., *Am J Gastroenterol* 71: 490-495, 1979.

tGLVP has been clinically tested in bleeding from esophageal varices at doses of up to 100 microg/kg day, and mortality from a bleeding episode was about 70% in untreated (with tGLVP) cases, only 13% in cases treated with tGLVP. See Vosmik et al., *Gastroenterology*, 72: 605-609, 1977.

B. Management of Uterine Bleeding: Menorrhagia, Metrorrhagia, Post-Partum Blood Loss tGLVP also shows a marked and prolonged vasoconstrictor effect lowering blood flow to the entire uterus in animals, see Cort et al., *Europ. J. Clin. Invest* 5:165, 1975 and has been clinically tried in uterine blood loss with success (Pavlin, et al., *Brit. J. Obstet. Gynaec.* 85:801-805, 1978).

C. Management of Bleeding During Abdominal Surgery

Excessive venous bleeding clouding the operative field in abdominal surgery can be dried up with a single 1 mg i.v. dose of tGLVP., Vosmik et al, *Gastroenterology*, ibid.

D. Management of Hemorrhagic Shock

In a number of animal models, including dogs, monkeys, rats, rabbits, in which controlled hemorrhage was carried out, treatment with tGLVP significantly increased survival time. See J. H. Cort,: "The Pharmacology and some clinical uses of Glypressin", registration report to the Czechoslovak Ministry of Health, 1975.

E. Management of Burns

This same survival prolongation effect in experimental burns was demonstrated in the same report as above (Cort, 1975) in rabbits treated with tGLVP.

As will be apparent from the following exemplary data, the hormonogen peptides of the invention are useful for minimization or prevention of visceral bleeding, gastrointestinal bleeding, uterine bleeding, hemorrhagic shock, burns, hematuria, interference with the course of gravidity, pancreatic disease, control of abdominal and gynecological bleeding during surgery and control of excessive ulcerogenic bleeding. This management is based upon the splanchnic blood vessel constrictor or pressor effects of long duration shown by the hormonogen polypeptides of the invention. Compared with the known vasopressin hormonogen tGLVP, examples of the invention show a striking increase in the potency and duration of visceral pressor action in in vivo animal model tests. Especially preferred hormonogens for these purposes are those wherein the peptide side chain is Gly, Gly-Gly, Gly-Gly-Gly and Leu.

Although the use of the hormonogens of the invention, dosage and route of administration will ultimately depend upon the patient's unique condition, and the judgment of his attending physician, they can generally be administered to the patient being treated at dosages and by routes calculated to deliver effective amounts of hormonogen to the site of action. For example, they may be administered by intravenous injection, infusion, parenteral injection, or subcutaneous injection or they may be administered intranasally in the form of nose drops.

With these routes of administration, the hormonogen can be administered as a dispersion or in solution in a suitable liquid medium, such as water, saline, isotonic aqueous solution and alcohol. The medium may contain various pharmaceutical carriers and additives generally such as physiological salts, anticlotting agents, dispersing agents, acidifying agents and the like. A preferred medium is physiological saline solution. The dispersion or solution is preferably acidic, having a pH of from about 3 to about 5, and especially about 4, to stabilize the hormonogen. If the formulation is for multiple use, it is also desirable to include in the dispersion or solution a small amount of a physiologically acceptable bacteriostat, e.g., chlorobutanol, to minimize bacterial contamination. This is especially useful in the intranasal preparation.

The concentration of the hormonogen in the solution is not narrowly critical, and can range from about 1 microg/ml to 1 mg/ml or higher, depending upon the intended mode of administration and dosage. In general, solutions intended for intranasal applications will contain higher concentrations than solutions intended to be administered by injection. Thus, solutions for intranasal administration ordinarily will contain from about 100 to about 400 microgram of hormonogen per milliliter, whereas injectable solutions will contain of the order of about 10 to about 40 microgram per milliliter.

The dosage of the hormonogen which is administered will depend greatly upon the specific action(s) of the hormonogen, the level(s) of such action(s), the effect intended, and the mode of administration. For example, when administered in the form of nose drops, the applied dosage must be about 10 times the applied dose administered by the intravenous route.

The following examples will illustrate the synthesis of N-substituted analogs in accordance with the invention. The examples are intended as illustrations the invention and are not to be taken as limitations thereof. All temperatures are in degrees Celsius unless otherwise noted.

EXAMPLE I

1-Desamino-[2-Phe, 8-Lys-N$^\epsilon$(Gly)]-Vasopressin
(A=H; B=Phe; E=Pro; FNH=L-Lys; G=—S—S—; X=Gly)

A 3.0-gram portion of benzhydrylamine-HCl resin (Beckman), having 0.51 milliequivalents of available amine per gram of resin, was placed in the 135-ml reaction vessel of a Vega Model 96 automatic, programable synthesizer. The peptide chain was built up by reacting, in sequence, the N$^\alpha$-(t-butyloxy-carbonyl) [N$^\alpha$-(t-Boc)] derivatives of Gly, N$^\epsilon$-(carbobenzoxy) Lys, Pro, S-(p-methoxybenzyl) Cys, Asn, Gln, Phe and S-(p-methylbenzyl)-$\beta$-mercaptopropionic acid, to form 4.52 grams of the resin-bonded peptide S-p-MeBzl-$\beta$-mercaptopropionic acid-Phe-Phe-Gln-Asn-S-p-MeOBzlCys-Pro-Lys (CBZ)-Gly-NH$_2$-Resin, representing an overall yield of 87 percent. The t-Boc amino acids all were obtained from Vega Laboratories, Inc. and were dissolved in appropriate solvents: the t-Boc derivatives of p-MeOBzlCys, Gly, Pro and Phe were dissolved in dichloromethane while those of Asn and Gln were dissolved in dimethylformamide (DMF) and a 2-fold excess of hydroxybenzotriazole monohydrate (HOBzt). The synthesis was performed according to the schedules set forth in Tables 1 and 2, employing 3-fold molar excess double couplings for each of the protected residues. In all cases, the resin was negative for free amino groups after the second coupling, as determined by the method of Kaiser et al., *Anal. Biochem.*, 34, 595 (1970).

TABLE 1

Coupling Scheme for Residues 8, 7, 6, 3, 2 and 1

| | | Reaction Condition | | |
|---|---|---|---|---|
| Step | Reagent | Vol. (ml) | Duration (min.) | Number of Repetitions |
| 1 | Dichloromethane | 50 | 0.5 | 5 |
| 2 | 50% Trifluoroacetic acid in dichloromethane | 50 | 2.0 | 1 |
| 3 | 50% Trifluoroacetic acid in dichloromethane | 50 | 30.0 | 1 |
| 4 | Dichloromethane | 50 | 0.5 | 5 |
| 5 | 2-Propanol | 35 | 0.5 | 2 |
| 6 | Dichloromethane | 50 | 0.5 | 5 |
| 7a | 5% Di-isopropyl-ethylamine in dichloromethane | 35 | 2.0 | 3 |
| 8 | Dichloromethane | 50 | 0.5 | 5 |
| 9b | Amino Acid in dichloromethane | 15 | 2.0 | 1 |
| 10 | Dicyclohexylcarbo-diimide (DCC) in dichloromethane | 15 | 30.0 | 1 |
| 11 | Dichloromethane | 50 | 0.5 | 5 |
| 12 | 2-Propanol | 35 | 0.5 | 2 |
| 13 | Dichloromethane | 50 | 0.5 | 2 |
| 14 | 2-Propanol | 35 | 0.5 | 2 |
| 15c | Dichloromethane | 50 | 0.5 | 5 | a - The sequence was started at this step for the initial coupling of Gly to the resin.
b - The vessel was drained after this step.
c - Steps 9-15 were repeated for the second coupling to increase yield.

Amino acids were t-Boc derivatives in 3.0M excess in solution. DCC was equimolar with protected amino acids.

TABLE 2

Coupling Scheme for Residues 5 and 4 in DMF

| | | Reaction Conditions | | |
|---|---|---|---|---|
| Step | | Vol. (ml) | Duration (min.) | Number of Repetitions |
| 1-8 | are identical with those of Table 1. | | | |
| 9 | 2-Propanol | 35 | 0.5 | 2 |
| 10 | Dichloromethane | 50 | 0.5 | 5 |
| 11a | Dimethylformamide | 35 | 2.0 | 3 |
| 12b | Amino Acid/HOBzt/DMF | 15 | 2.0 | 1 |
| 13 | Dicyclohexyl carbodiimide (DCC) in dimethyl-formamide | 15 | 120.0 | 1 |
| 14 | Dimethylformamide | 35 | 0.2 | 1 |
| 15 | Dichloromethane | 50 | 0.5 | 5 |
| 16 | 2-Propanol | 35 | 0.5 | 2 |
| 17 | Dichloromethane | 50 | 0.5 | 2 |
| 18 | 2-Propanol | 35 | 0.5 | 2 |
| 19 | Dichloromethane | 50 | 0.5 | 5 | a - For the second coupling steps 11-19 were repeated.
b - The vessel was not drained after this step. Amino acids were t-Boc derivatives in 3.0-fold molar excess in DMF. HOBzt was used in a 2-fold molar excess over amino acid concentrations. DCC was equimolar.

A 400-mg sample of the thus-obtained peptide resin was placed in a 50 ml Teflon-Kel-F vessel in the HF apparatus supplied by Peninsula Laboratories, and a small Teflon-coated magnet stirring bar and 1 ml of anisole were added. A frit was secured near the top of the vessel, which was then attached to the HF apparatus. The latter was evacuated with a vacuum pump and the sample vessel was immersed in a dry ice/acetone bath. After 20 minutes the sample vessel was disconnected from the vacuum and connected to the HF reservoir. HF was distilled into the vessel until the total liquid volume was about 10 ml (over about 5 minutes). The dry ice/acetone bath was replaced by a water/ice bath, a magnetic stirrer was placed underneath the vessel and the latter was sealed off from the rest of the system. After 75 minutes, the vessel was carefully opened to the pump and HF was allowed to evaporate over about 60 minutes. The sample vessel remained immersed at 0° C. throughout this time. The system was then filled with nitrogen to atmospheric pressure and the cleavage vessel was quickly removed and sealed with parafilm.

The material was washed out of the vessel into a coarse-fritted funnel with several portions of degassed ethyl acetate (totaling about 100 ml). The funnel and vessel were then placed in a vacuum dessicator and evacuated for 30 minutes to remove the remaining ethyl acetate. The cleavage vessel and the resin in the funnel were then washed with several portions of degassed 1M acetic acid (100 ml total) followed by 300 ml of degassed water in several portions. The solution was then adjusted to pH 6.9 with 3M aqueous ammonia, and 25 ml of 0.01M potassium ferricyanide solution were added. The yellow solution was stirred for about 30 minutes, the pH was then adjusted to 5 with 50% acetic acid and AG-3 anion exchange resin (TFA form) was added and the mixture was stirred for a further 20 minutes. The slurry was then filtered, yielding a clear colorless solution and the resin was washed with a small portion of water. The solution was then freeze-dried.

The resulting powder was taken up in about 15 ml of 50% acetic acid and filtered, yielding a clear pale yellow solution that was applied to a Sephadex G-15 column (2.6×90 cm) previously equilibrated with 50% acetic acid. Elution was at a rate of 1 ml/min. and 3-ml fractions were collected. Two overlapping peaks were eluted by detecting at $OD_{265}$. Peak 1 retained a slight yellow color and appeared in fractions 45–53 and peak 2 appeared in fractions 54–79. Peak 2 material was rechromatographed under identical conditions and the second peak was the desired product, 1-desamino-[2-Phe, 8-Lys]-vasopressin, in a yield of 62.5 mg. Amino acid analysis after 24 hour hydrolysis in 6M HCl was Lys 1.1, Gly 1.0, Pro 1.0, Glu 1.2, Phe 1.8, Asp 1.0, hemi-Cys (not reliable after HCl hydrolysis) 0.6. TLC of peak 2 material:

| Solvent System | Results* | Rf |
|---|---|---|
| 1-butanol-acetic acid-water (4:1:5, upper phase) | one spot | 0.43 |
| 1-butanol-acetic acid-pyridine-water (15:3:10:12) | one spot | 0.70 |
| ethyl acetate-pyridine-acetic acid-water (5:5:1:3) | one spot | 0.90 |

*Visualization by ninhydrin. O-Toluidine did not reveal additional spots.

To a solution 50 mg of 1-desamino-[2-Phe, 8-Lys]-vasopressin in DMF (1 ml), were added triethyl amine (0.007 ml) followed by N-t-Boc-glycine p-nitrophenyl ester (69 mg) and 1-HOBzt (10 mg). After 1.5 hour stirring at room temperature, all of the peptide had reacted, as judged by TLC on silica gel ($CHCl_3$-MeOH-$H_2O$, 200:75:13) using ninhydrin visualization. The reaction mixture was then diluted with 2-propanol (10 ml) and ether (50 ml), cooled to 4° C. and filtered. The product was triturated with hot acetone (15 ml), diluted with cold ether (50 ml) and collected by centrifugation. The yield was 38 mg. The protected decapeptide was deprotected in trifluoroacetic acid (1 ml) over 30 minutes and isolated by centrifugation after ether precipitation. Final yield of 1-desamino-[2-Phe, 8-Lys-$N^\epsilon$(Gly)]-vasopressin was 29.14 mg (54.5%).

Amino acid analysis: (24 hour hydrolysis in 6M HCl) Lys 1.0, Asp 1.0, Glu 1.0, Pro 0.9, Gly 2.1, Phe 1.7, hemi-Cys 0.6.

| TLC: Solvent System | Major Component Rf |
|---|---|
| 1-butanol-acetic acid-water (4:1:5, upper phase) | 0.37 |
| 1-butanol-acetic acid-pyridine-water (15:3:10:12) | 0.74 |
| ethyl acetate-pyridine-acetic acid-water (5:5:1:3) | 0.84 |

Visualization was with ninhydrin. O-Toluidine did not reveal additional spots.

EXAMPLE II

1-Desamino-[8-Lys-$N^\epsilon$(Gly-Gly-Gly)]-Vasopressin
(A=OH; B=Phe; E=Pro; FNH=L-Lys;
G=—S—S—; X-Gly-Gly-Gly)

Employing procedures similar to those described in Example I, except that tyrosine (Tyr) was substituted for phenylalanine (Phe) at position 2, 1-desamino-[8-Lys]-vasopressin was synthesized. Amino acid analysis: Lys 1.0, Asp 1.0, Glu 1.0; Pro 0.9, Gly 0.9, Tyr 1.1, hemi-Cys 0.7.

A 2.98-gram portion of Gly-Gly-Gly (Vega Laboratories, Inc.) was suspended in 100 ml of 50% dioxane and the pH was adjusted to about 10.0 with dissolution of the suspended material. The 2.2 grams of di-t-butyl-dicarbonate were added, and the reaction was followed by TLC (butanolpyridine-acetic acid-water, 15:10:3:6). After three hours an additional 1-gram portion of di-t-butyl-dicarbonate was added, and after an additional three hours the reaction was complete for protecting the N-terminal of the tripeptide. The solution was then extracted three times with 30-ml portions of hexane. The aqueous phase was adjusted to pH 2.5 and then extracted three times with 50-ml portions of ethyl acetate, dried over $MgSO_4$ and concentrated to an oil. The residue was crystallized from ethyl acetate-ether. The yield was 750 mg. This material was converted to N-t-Boc-Gly-Gly-Gly p-nitrophenyl ester in the usual manner to yield 750 mg of the ester.

Employing procedures similar to those described in Example I, the N-t-Boc-Gly-Gly-Gly p-nitrophenyl ester was coupled to the omega amino group of the 8-Lys peptide residue and the N-t-Boc group was then removed to yield 1-desamino-[8-Lys-$N^\epsilon$(Gly-Gly-Gly)]-vasopressin. Amino acid analysis: Lys 1.0, Asp 1.0, Glu 1.0, Pro 0.9, Gly 3.8, Phe 1.0, Tyr 1.1, hemi-Cys 0.6.

EXAMPLE III

1-Desamino-1-monocarba-[7-thioPro, 8-Lys-$N^\epsilon$(Leu)]-Vasopressin (A=OH; B=Phe; E=4-thioPro; FNH=L-Lys; G=$CH_2S$; X=Leu)

Employing procedures similar to those described in Example I, except that 4-thioPro is substituted for Pro, N-t-Boc-S-$\beta$-ethoxycarbonyl-butylcysteine is substituted for N-t-Boc-S-p-MeOBzl-Cys, and Leu is substituted for Gly in the side chain, 1-desamino-1-monocarba-[7-thioPro, 8-Lys-$N^\epsilon$(Leu)]-vasopressin can be produced, using the following exceptions in the order of coupling:

(1) 4-thio-Pro is substituted for Pro in sequence number 7 (Table 1) (3rd coupling).

(2) The N-t-Boc-S-$\beta$-ethoxycarbonylbutylcysteine is substituted for N-t-Boc-S-p-MeOBzl-Cys in sequence position 6 (Table 1) (4th coupling).

(3) The final (9th) coupling of S-p-MeO-Bzl-$\beta$-mercaptopropionic acid is omitted, along with the ring closure procedure using potassium ferricyanide.

(4) Ring closure by formation of an amide bond between residue 6 and N-t-Boc-Tyr in sequence position 2 is carried out by the procedure of Jost. K.: Collect. Czech. Chem. Commun., 36, 218 (1971) with the peptide still attached to the resin.

(5) The peptide is then cleaved off the resin using HF in the same manner as described in Example I.

(6) Following purification on Sephadex G-15, N-t-Boc-Leu is coupled to the omega N of the 8-Lys peptide residue in the same manner as outlined for Gly coupling in Example I, and the final Leu protecting group is removed, also in the same manner as described in Example I.

EXAMPLE IV

1-Desamino-[2-Phe, 8-Lys-N$^\epsilon$(Gly-Gly-Gly)]-Vasopressin (A=H; B=Phe; E=Pro; FNH=L-Lys; G=—S—S—; X=Gly-Gly-Gly)

Employing procedures similar to those described in Example I, except that the Gly-Gly-Gly chain is substituted for the Gly substituent on the Lys peptide as described in Example II, 1-desamino-[2-Phe, 8-Lys-N$^\epsilon$(Gly-Gly-Gly)]-vasopressin may be produced.

EXAMPLE V

1-Desamino-[8-D-Lys-N$^\epsilon$(Gly-Gly-Gly)]-Vasopressin (A=OH; B=Phe; E=Pro; FNH=D-Lys; G=—S—S—; X=Gly-Gly-Gly)

Employing procedures similar to those described in Example I, except that tyrosine (Tyr) is substituted for phenylalanine (Phe) at position 2, D-Lys is substituted for L-Lys at position 8, and the Gly-Gly-Gly tripeptide chain is substituted for Gly as the 8-Lys-N$^\epsilon$ substituent as described in Example II, 1-desamino[8-D-Lys-N$^\epsilon$(Gly-Gly-Gly)]-vasopressin is produced.

EXAMPLE VI

1-Desamino-[2-Phe, 8-Orn-N$^\epsilon$(Gly)]-Vasopressin (A=H; B=Phe; E=Pro; FNH=L-Orn; G=—S—S—; X=Gly)

Employing procedures similar to those described in Example I, except that ornithine (Orn) is substituted for lysine (Lys) at position 8, there is produced 1-desamino-[2-Phe, 8-Orn -N$^\epsilon$(Gly)]-vasopressin.

EXAMPLE VII

1-Desamino-[2-Phe, 7-3,4-dehydroPro, 8-Lys-N$^\epsilon$(Gly)]-Vasopressin (A=H; B=Phe; E=3,4-dehydroPro; FNH=L-Lys; G=—S—S—; X=Gly)

Employing procedures similar to those described in Example I, except that 3,4-dehydroproline (3,4-dehydroPro) is substituted for Pro in position 7, there is produced 1-desamino-[2-Phe, 7-3,4-dehydro, 8-Lys-N$^\epsilon$(Gly)]-vasopressin.

EXAMPLE VIII

1-Desamino-[8-Lys-N$^\epsilon$(Gly-Gly)]-Vasopressin (A=OH; B=Phe; E=Pro; FNH=L-Lys; G=—S—S—; X=Gly-Gly)

Employing procedures similar to those described in Example I, except that tyrosine (Tyr) was substituted for phenylalanine (Phe) at position 2, 1-desamino-[8-Lys-N$^\epsilon$(Gly-Gly)]-vasopressin was synthesized. Amino acid analysis: Lys 1.07, Asp 1.01, Gln 0.94, Pro 1.00, Gly 2.99, Tyr 0.98, hemi-Cys present.

The N-substituted hormonogens of this invention, as represented by Formula I, when administered to mammals, are believed to be "activated" by cleavage of the peptide side chain to release the active 1-desamino vasopressin analog which will still possess its original activity. There is no other apparent explanation for the striking increase in pressor response duration shown in Table 3, which follows on page 24, including the fact that the greater the number of amino acid residues in the peptide side chain, the greater the prolongation of the response. Thus, for example, the analogs of this invention, wherein A is hydrogen or hydroxyl; B is Phe; E is Pro; FNH is L-Lys or L-Orn; and G is —S—S—, —CH$_2$S— or —SCH$_2$—; such as the compounds of Examples I, II and VIII can be expected to have prolonged pressor activity, and have utility in the treatment of shock, gastointestinal bleeding, uterine bleeding, burns, interference with the course of gravidity, hematuria and pancreatic diseases. For such compounds, X is preferably Gly, Gly-Gly, Gly-Gly-Gly or Leu.

Moreover, the hemodynamic responses of 1-desamino N-substituted hormonogens of the invention show a greater potency (about five times greater), a greater duration (about four times greater half-life of the pressor response) and greater efficiency of delivery of active nonapeptide to receptors than tGLVP shows. In terms of the peak potencies and response duration shown by Tables 3 and 4 which follows on pp. 24 and 25, the tested hormonogens of this invention are about 20 times more effective in achieving pressor action than the triglycyl N-LVP hormonogen, tGLVP.

Pressor assays of the compounds of Examples I, II and VIII were carried out in 200 g body weight, male Sprague-Dawley rats using the techniques reported by Schaechtelin et al in "Enhancement of the Activity of Angiotensin II by Certain Cations", *Molec. Pharmacol.*, 10, 57–67 (1974) with calibration of responses against a 3-point curve using purified lysine-vasopressin (LVP) or 1-desamino-lysinevasopressin (dLVP), both calibrated against international standard LVP. The half-lives of the responses were compared to the standard LVP at equi-peak-potent levels. The results of these tests are summarized in Table 3, which follows.

TABLE 3

| | Evaluation of Pressor Activity | |
|---|---|---|
| Compound | Peak Potency IU/mg | Ratio of Half-Life of Compound to Standard |
| Example I | 1.9 | 12.5 |
| Example II | 5.4 | 37–53 |
| Example VIII | 5.6 | 15–20 |
| dLVP standard | 270 | 1.0 |
| tGLVP | 1.2 | 11.5 |

From the data summarized in Table 3, it can be seen that the polypeptides of Examples I, II and VIII possess prolonged pressor activity of higher potency compared to that of tGLVP.

tGLVP has been shown in animals and patients to control gastric mucosal hemorrhage due to vasoconstriction in the arterial bed supplying the stomach, including peptic ulcer bleeding. The hormonogen of Example II has been tested in an animal model for peptic ulcer bleeding to study such effects. The test was conducted on heparinized paired control-experimental rats in which a 1 mm squared lesion was created in the exteriorized, open stomach near to the pylorus. Controls were untreated, experimentals were pretreated with 2.5 ug/kg i.v. just before the lesion was cut out. It should be stressed that the effective dose of tGLVP in gastric mucosal bleeding is in the range 20–50 microg/kg. In the present experiment bleeding was followed for 45 min. after lesioning. At this low dose, the polypeptide of Example II brought about a decrease in bleeding compared with controls. The data are summarized in Table 4 which follows.

TABLE 4

Gastric Hemostasis[1,2] by the polypeptide of Example II in Heparinized Rats

| Time after Dosing (min.) | Dose (microg/Kg) | |
| --- | --- | --- |
| | 0 | 2.5 |
| 6–10 | 3.63 ± 0.48 | 1.24 ± 0.62 |
| 11–15 | 3.81 ± 0.37 | 1.04 ± 0.52 |
| 16–20 | 3.92 ± 0.14 | 1.29 ± 0.60 |
| 21–25 | 3.29 ± 0.45 | 1.70 ± 0.82 |
| 26–30 | 3.00 ± 0.84 | 1.75 ± 0.85 |
| 31–35 | 2.94 ± 0.62 | 1.81 ± 1.00 |
| 36–40 | 2.71 ± 0.70 | 1.43 ± 0.4 |

[1]Mean bleeding rate scores: 0 = no bleeding; 1 = oozing; 2 = slight bleeding; 3 = moderate bleeding; 4 = heavy bleeding.
[2]Means and standard deviations recorded. All responses to 2.5 ug/kg dose are different from the control within the period ($p < .05$).

As shown by Cort et al. *Europ. J. Clin Invest*, ibid, and Wolfson et al., *Am. J. Gastroenterol*, ibid, tGLVP causes marked decreases in blood flow to the uterus and pancreas of cats and dogs. These same effects have also been shown in man. Using the organ distribution of i.v. injected 86 Rb (see Cort et al. *Europ J Clin Invest*) as a measure of blood flow, the polypeptide of Example II, given i.v. over the range 2–50 microg/kg, also produced marked changes in the same direction in the same organs, these being statistically significant. These experiments were carried out in 65 Sprague-Dawley rats anesthethized with urethane.

Also, as shown by Cort et al. *Europ J. Clin. Invest.*, tGLVP in rats caused a marked and prolonged decrease in blood flow to the entire gut from the lower third of the esophagus to the rectum. Five unanesthetized dogs received the polypeptide of Example II by infusion at the rate of 1.0 microg/kg. min. or half that, and variously radioactively labelled glass microspheres were used to measure organ blood flows before and 10 and 30 min after the end of the infusion (all catheters had been surgically implanted beforehand). There were very marked and prolonged decreases in blood flow to the skin, 70–80% decreases to the esophagus and stomach (all parts). On the other hand, there were moderate increases in blood flow to liver and brain. In short, as far as has been determined, the range of hemodynamic actions caused by tGLVP is also caused by the polypeptide of Example II, but the latter is about 5 times as potent and 4 times as prolonged in action.

What is claimed is:

1. A polypeptide represented by the formula

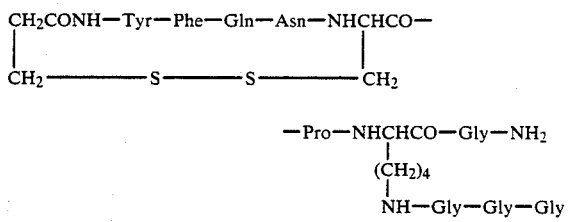

wherein the stereoconfiguration of the lysine moiety at the 8 position is D or L.

2. 1-Desamino [(N-ε-Triglycyl)-8-L-lysine]vasopressin according to claim 1.

3. A pharmaceutical composition which comprises a pharmaceutical carrier in combination with an effective amount of a polypeptide according to claim 1.

4. A method for the treatment of a patient having gastrointestinal bleeding including bleeding peptic ulcers, which comprises administering to the patient an effective amount of a polypeptide according to claim 1 either alone or in combination with a pharmaceutical carrier.

5. A method for the treatment of a patient suffering from uterine bleeding, which comprises administering to the patient an effective amount of a polypeptide according to claim 1 either alone or in combination with a pharmaceutical carrier.

6. A method for the treatment of bleeding during abdominal or gynecological surgery on a patient, which comprises administering to the patient an effective amount of a polypeptide according to claim 1 either alone or in combination with a pharmaceutical carrier.

7. A method for the management of the blood pressure of a patient suffering from burns or hemorrhagic shock, which comprises administering to the patient an effective amount of a polypeptide according to claim 1 either alone or in combination with a pharmaceutical carrier.

* * * * *